United States Patent
Jones et al.

(10) Patent No.: US 11,980,734 B2
(45) Date of Patent: May 14, 2024

(54) MULTI-LUMEN COUPLER FOR FLUID TRANSFER

(71) Applicant: Avasys, LLC, Columbia, MD (US)

(72) Inventors: Cameron C. Jones, Columbia, MD (US); Alex Driver, Cambridge (GB); Grant Smetham, Cambridge (GB); Clifford R. Weiss, Baltimore, MD (US)

(73) Assignee: Avasys, LLC, Columbia, MD (US)

( * ) Notice: Subject to any disclaimer, the term of this patent is extended or adjusted under 35 U.S.C. 154(b) by 389 days.

(21) Appl. No.: 17/188,446

(22) Filed: Mar. 1, 2021

(65) Prior Publication Data
US 2021/0275792 A1  Sep. 9, 2021

Related U.S. Application Data

(60) Provisional application No. 62/984,443, filed on Mar. 3, 2020.

(51) Int. Cl.
*A61M 39/10* (2006.01)

(52) U.S. Cl.
CPC ....... *A61M 39/105* (2013.01); *A61M 2207/00* (2013.01)

(58) Field of Classification Search
CPC ........ A61M 39/105; A61M 2039/0673; A61M 2039/082; A61M 2039/1077; A61M 39/12; A61M 39/28; A61M 39/285–287
See application file for complete search history.

(56) References Cited

U.S. PATENT DOCUMENTS

| | | | |
|---|---|---|---|
| 4,950,255 A * | 8/1990 | Brown | A61M 39/284 604/533 |
| 5,478,331 A | 12/1995 | Heflin et al. | |
| 5,749,861 A | 5/1998 | Guala et al. | |
| 6,156,025 A | 12/2000 | Niedospial, Jr. et al. | |
| 6,572,590 B1 | 6/2003 | Stevens et al. | |
| 6,719,727 B2 | 4/2004 | Brimhall et al. | |
| 6,827,710 B1 | 12/2004 | Mooney et al. | |
| 6,872,198 B1 | 3/2005 | Wilson et al. | |
| 6,921,396 B1 | 7/2005 | Wilson et al. | |
| 6,969,381 B2 | 11/2005 | Voorhees | |
| 7,063,685 B2 | 6/2006 | Rome | |
| 7,094,218 B2 | 8/2006 | Rome et al. | |
| 7,117,892 B2 | 10/2006 | Krywitsky | |
| 7,153,296 B2 | 12/2006 | Mitchell | |
| 7,163,531 B2 | 1/2007 | Seese et al. | |
| 7,182,746 B2 | 2/2007 | Haarala et al. | |
| 7,261,708 B2 | 8/2007 | Raulerson | |
| 7,306,197 B2 | 12/2007 | Parrino et al. | |
| 7,343,931 B2 | 3/2008 | Packham | |
| 7,347,853 B2 | 3/2008 | DiFiore et al. | |
| 7,377,915 B2 | 5/2008 | Rasmussen et al. | |
| 7,566,077 B2 | 7/2009 | Tsurumi | |
| 7,578,803 B2 | 8/2009 | Rome et al. | |
| 7,857,284 B2 | 12/2010 | Kimball et al. | |
| 7,878,553 B2 | 2/2011 | Wicks et al. | |

(Continued)

*Primary Examiner* — Theodore J Stigell
(74) *Attorney, Agent, or Firm* — Mintz, Levin, Coh, Ferris, Glovsky, Popeo, P.C.

(57) ABSTRACT

A multi-lumen coupler for fluid transfer with a plurality of attachable members is provided. The multi-lumen coupler allows the attachment and detachment of various members used for fluid transfer to an elongated percutaneous medical article such as a catheter or cannula, during use with a patient.

22 Claims, 13 Drawing Sheets

(56) References Cited

U.S. PATENT DOCUMENTS

| | | |
|---|---|---|
| 7,959,192 B2 | 6/2011 | Elton et al. |
| 8,113,546 B2 | 2/2012 | Jensen et al. |
| 8,177,760 B2 | 5/2012 | Rome et al. |
| 8,177,771 B2 | 5/2012 | Butts et al. |
| 8,397,756 B2 | 3/2013 | Packham et al. |
| 8,454,579 B2 | 6/2013 | Fangrow, Jr. |
| 8,540,685 B2 | 9/2013 | Moorehead et al. |
| 8,715,222 B2 | 5/2014 | Truitt et al. |
| 8,795,256 B1 | 8/2014 | Smith |
| 9,186,494 B2 | 11/2015 | Fangrow |
| 9,279,530 B2 | 3/2016 | Schmidt |
| 9,364,653 B2 | 6/2016 | Williams et al. |
| 9,506,590 B2 | 11/2016 | Wilhelm et al. |
| 9,616,196 B2 | 4/2017 | Haarala et al. |
| 10,267,445 B2 | 4/2019 | Ira et al. |
| 2007/0108761 A1 | 5/2007 | Ko et al. |
| 2008/0009832 A1 | 1/2008 | Barron et al. |
| 2008/0097296 A1 | 4/2008 | Pepin |
| 2008/0277002 A1 | 11/2008 | Hendrixson |
| 2009/0137944 A1 | 5/2009 | Haarala et al. |
| 2011/0006520 A1* | 1/2011 | Hall .................... A61M 39/00 285/383 |
| 2016/0030387 A1 | 2/2016 | Winnicki |

\* cited by examiner

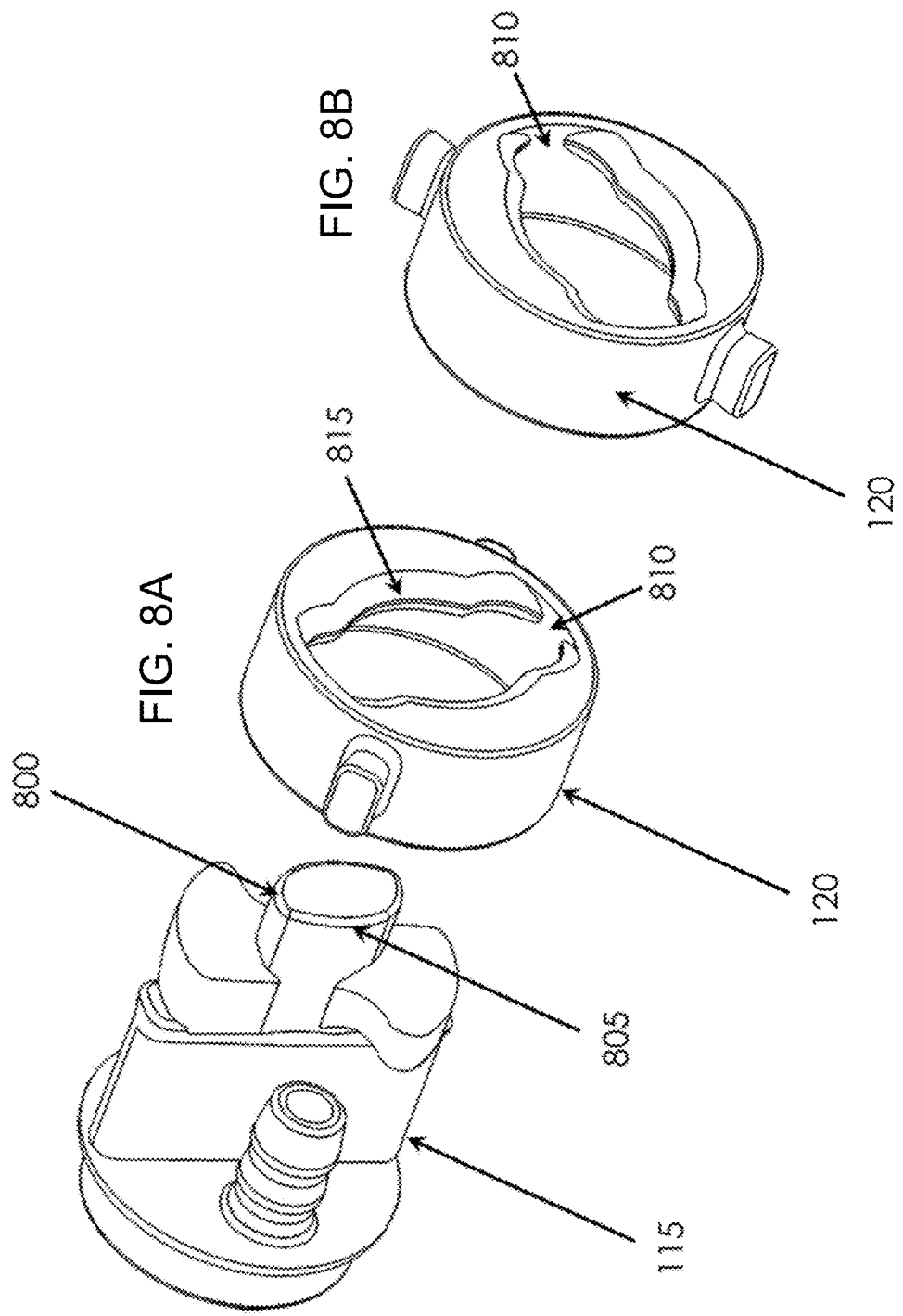

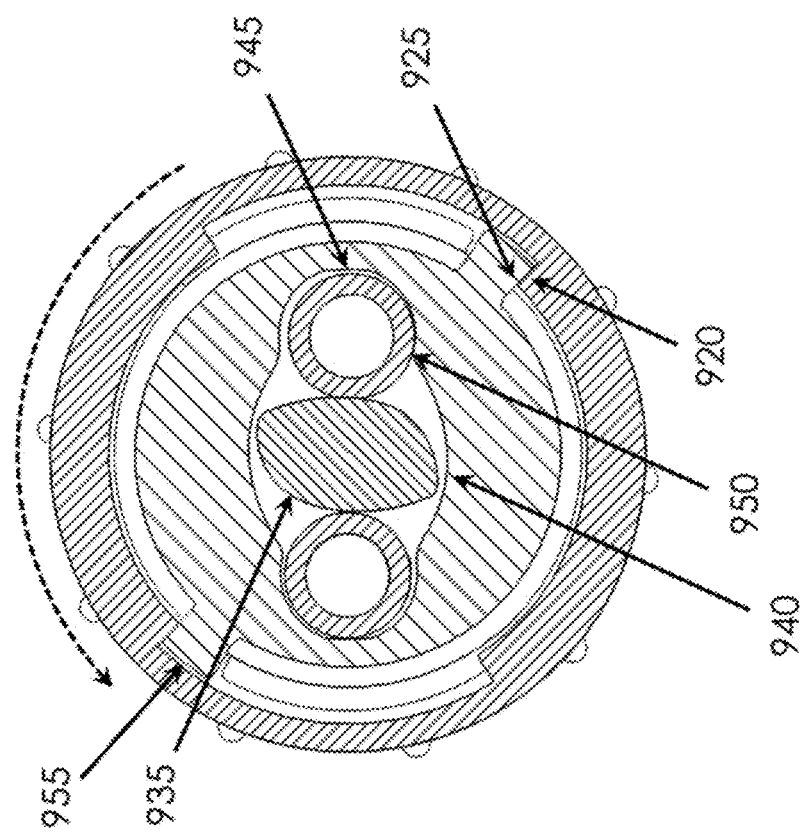

MULTI-LUMEN COUPLER FOR FLUID TRANSFER

CROSS-REFERENCE TO RELATED APPLICATIONS

This Application claims the benefit of U.S. Provisional Application 62/984,443 filed on Mar. 3, 2020. This entire contents of these applications are incorporated herein by reference in their entirety.

FIELD OF INVENTION

The present invention relates generally to medical devices. More particularly, the present invention relates to a coupling system for use with a catheter.

BACKGROUND

Many patients with chronic diseases or who are critically ill require frequent administration of fluids for nutritional or medicinal purposes. These medications are oftentimes delivered through an intravenous catheter such as a central venous catheter (CVC), peripherally inserted central line (PICC), or midline catheter, which provides vascular access and may be kept in place for durations lasting several days up to several months.

In most instances, the patient is not receiving a continuous infusion of fluids through the catheter for the entire duration in which the catheter is implanted. For example, patients requiring dialysis may visit a healthcare clinic for a few hours each week for scheduled infusion therapy, but outside of these dialysis sessions, the catheter is unused while remaining indwelling to the patient for future visits. During such times of non-use, a distal portion of the catheter is sealed to prevent fluid movement and protect against air and external pathogens from entering the catheter, which may lead to clinical adverse events.

Many modern medical catheters are multi-luminal (i.e., two or more individual channels running longitudinal inside a single extruded catheter body) and manufactured from polymeric materials such as silicone, polyethylene, polyurethane, and polytetrafluorethylene. When a catheter is designed for percutaneous use (i.e., a portion of the implanted catheter remains outside the body of the patient), the external portion consists of an interface for connecting external medical articles to the implanted catheter. Traditionally, the external interface is a standard medical fitting, such as a Luer connector, attached to a single lumen extension tube continuous with a fluid lumen of the implanted catheter. For multi-lumen catheters, the distal, external interface is defined by multiple single lumen extension tube and Luer connector subassemblies—one corresponding to each of the lumens of the multi-lumen catheter—that converge into the multi-lumen catheter at a junction referred to as the catheter hub. In order to restrict fluid movement (and risk of air emboli) when a lumen of the implanted catheter is not being used, each single lumen extension tube is often clamped and a self-sealing valve or cap is attached to the Luer fitting to seal the distal fluid lumen opening.

While the catheter extension tube(s) facilitate access to the indwelling catheter by providing increased range of motion when connecting medical articles, the overall size and design of the external portion of the catheter can create challenges in patient care. The catheter extension(s) can become entangled in clothing, which can lead to tugging and possible displacement of the indwelling catheter tip from its intended clinical position; components on the extension subassembly such as clamps and Luer fittings can cause abrasions against the patient's skin and can be generally uncomfortable; and the terminal sites of fluid connectors may have surfaces that are difficult to thoroughly disinfect, which can lead to increased risk of infection and have a direct negative impact on patient care.

It would therefore be advantageous to provide a system that reduces the overall external load on percutaneous catheters, while facilitating the safe attachment and removal of various medical articles.

SUMMARY

The present invention provides a multi-lumen coupler for fluid transfer capable of achieving the above-described advantages.

In one aspect, a multi-lumen coupler (MLC) for fluid transfer is provided that comprises of a primary MLC assembly and an attachable secondary MLC assembly. The primary MLC assembly comprises of an outer housing defining a proximal end and a distal end. The distal end of the outer housing defines an opening into an inner space defined by the outer housing, and the proximal end of the housing defines a proximal connector for coupling to an intravenous catheter hub comprised of a single lumen extension or multiple fluid lumen extensions, whereby each single lumen extension(s) of the distal intravenous catheter is disposed between the proximal end and distal end of the primary MLC assembly. Additionally, disposed between the proximal and distal ends of the primary MLC assembly is an occluding mechanism that can block a section of the fluid channel of the single lumen extension(s). The attachable secondary MLC assembly comprises of a proximal end that connects to the distal end of the primary MLC assembly and a distal end that comprises of a standard fluid fitting such as a Luer connector.

In an additional aspect, the occluding mechanism of the primary MLC is a clamping mechanism that includes one or more clamping members that, together with a surface within the outer housing of the primary MLC assembly, occludes a region on the single lumen extension(s) of the intravenous catheter. The clamping member(s) is changed between an open (unclamped) and closed (clamped) state(s) by an action of the attachable secondary MLC assembly.

In another aspect, the attachable secondary MLC assembly comprises of multiple single lumen extension tubes, each corresponding to an individual fluid lumen of the primary MLC assembly. Accordingly, each single lumen extension tube consists of a proximal and distal end, where the distal end comprises of a standard fluid fitting such as a Luer connector, and the proximal end forms a fluid-tight seal with a corresponding lumen opening on the distal connector region of the primary MLC assembly. When the secondary MLC assembly comprises of two or more single lumen extension tubes, the proximal end of each single lumen extension tube is formed in a single connector interface, consisting of individual fluid lumens, which may be releasably engaged with the distal connector region of the primary MLC assembly by a mechanical system, thereby coupling each single lumen extension tube of the attachable secondary MLC assembly to a corresponding single lumen extension tube of the primary MLC assembly.

In an additional aspect, a mechanical system of the attachable secondary MLC assembly consists of one or more interlocking members for securing the attachable secondary MLC assembly to the primary MLC assembly.

In a further aspect, a mechanical system of the attachable secondary MLC assembly performs an action of opening or closing the clamping member(s) of the primary MLC assembly. Furthermore, the mechanical system may be designed to close the clamping member(s) prior to detachment of the attachable secondary MLC assembly in order to prevent fluid movement within the catheter upon removal of the secondary MLC assembly. Accordingly, the attachable secondary MLC assembly may be released from the primary MLC assembly while the proximal catheter unit is implanted in a patient.

In an additional aspect, the distal end of the attachable secondary MLC assembly includes a valve system integrated with the fluid fitting (e.g., Luer connector). In particular, the valve system may be of the form of a needleless connector, whereby attachment of a Luer connector to the valve system creates an open fluid channel between the attachable member (e.g., a syringe) and the distal end of the attachable secondary MLC assembly, upon removal thereof, results in the valve system closing the fluid channel of the attachable secondary MLC assembly. Therefore, the valve system of the attachable secondary MLC assembly may serve as an additional occluding mechanism to the MLC, whereby the attachable secondary MLC assembly may be attached to the primary MLC assembly in a configuration where the occluding mechanism of the primary MLC assembly is in an open (unclamped) state and fluid movement within the catheter is restrained.

In another aspect, the MLC includes an attachment member that connects to the distal end of the primary MLC assembly to seal the catheter while not in use. The attachment member specifically connects to a distal connector region of the primary MLC assembly and is secured by a locking member that engages with a protrusion formed on the primary MLC assembly.

According to yet another aspect of the present invention, a method is provided for releasably attaching a fluid coupler. The method includes affixing a catheter having a primary MLC assembly and occluding mechanism as described above to a surface of a patient and then blocking fluid movement within the catheter by an action of the attachable secondary MLC assembly before removing said attachable secondary MLC assembly. An attachable secondary MLC assembly can be attached to the catheter at a later time. The catheter is affixed to the patient surface by a securement device, suturing, or using an adhesive.

Notably, the present invention is not limited to the combination of catheter elements as listed above and may be assembled in any combination of the above-described elements. Moreover, references to multi-lumen devices are intended to be inclusive of single lumen catheters as well.

Other aspects of the invention are disclosed infra.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 8A-8B illustrate perspective views of various positions of the occluding mechanism;

FIGS. 9A-9C illustrate cross-sectional views of the occluding mechanism on a particular region disposed within the proximal and distal ends of the primary MLC assembly and the positional relationship of the occluding mechanism with respect to the actions of the attachable secondary MLC assembly according to an exemplary embodiment of the present invention;

DETAILED DESCRIPTION

Figure 1:
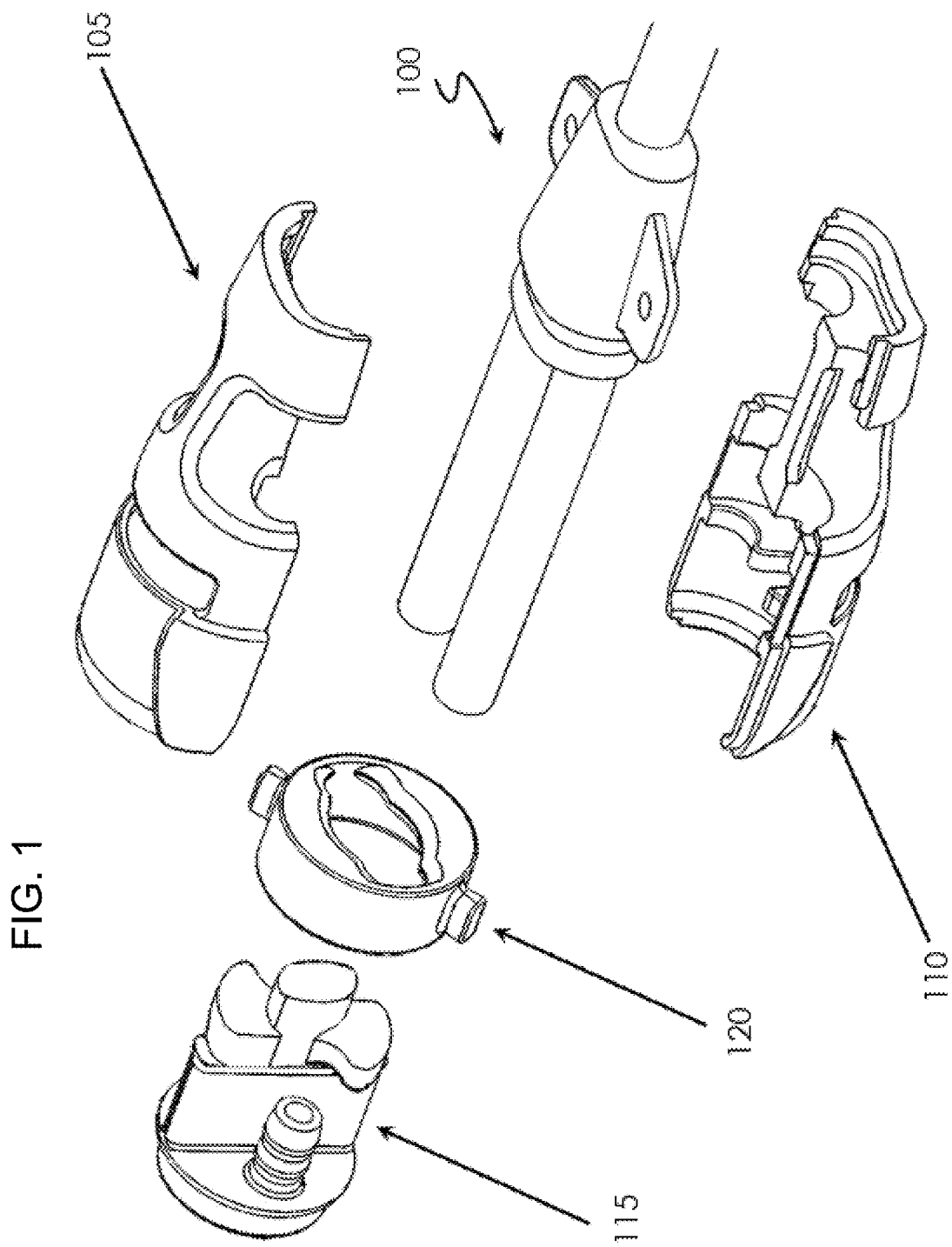
FIG. 1 illustrates an exploded view of the distal primary catheter assembly according to an exemplary embodiment of the present invention.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The presently disclosed subject matter will now be described more fully hereinafter with reference to the accompanying drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The present invention is directed to a fluid connection interface with a plurality of attachment members (i.e., members that are attachable to the fluid connection interface). More particularly, the present invention is directed to a technology that creates a coupling system between elongated medical devices such as catheters or cannulas, and attachable medical articles such as syringes and Luer access devices. The fluid connection interface is a coupling system that allows direct lumen connection(s) between the lumen(s) of the elongated medical device and the lumen(s) of an attachable medical article, where the attachable medical article may connect directly to the coupling interface of the elongated medical device through a matching coupling interface or via connecting to a secondary assembly which serves as an adapter between the medical article and the coupling interface. The coupling system contains an occluding mechanism that allows removal of the attachable medical article while restraining fluid movement in the elongated medical device. The coupling system is in proximity to the catheter hub and encloses each distal single lumen extension thereof to create a terminal connecting interface to the elongated medical device for connecting medical articles. Retaining the catheter hub allows the catheter to be secured using methods known in the art.

For the present invention, one example of an attachable member is a plurality of single lumen extensions, each with a distal Luer fitting, and each proximal end joined together in the form of the attachable fluid coupling interface (i.e., the attachable secondary assembly of the MLC). In particular, when the attachable secondary assembly is attached to the primary MLC of the elongated medical device, the full assembly resembles a common percutaneous catheter and can be inserted into a patient by one skilled in the art. Following clinical technique known by one of ordinary skill in the art, the implanted catheter may be checked for patency, flushed, and primed with a saline solution, and secured to the patient's skin through a preferred securement method. When the implanted catheter is not required for immediate clinical use (e.g., infusion) the attachable secondary assembly may be removed from the implanted catheter. Upon removal of the attachable secondary assembly, a cap may be attached to the primary MLC and the low profile extravascular portion of the catheter may be covered by a medical dressing or gauze to minimize entanglement with environmental articles.

FIG. 1 illustrates an exploded view of a distal primary catheter assembly according to an exemplary embodiment of the present invention. The primary catheter assembly may include a catheter subassembly 100 (discussed further in FIG. 6) and the components of the primary MLC assembly: the outer housing 105 and 110; the tube connector 115; and the occluding mechanism 120.

Figure 2:
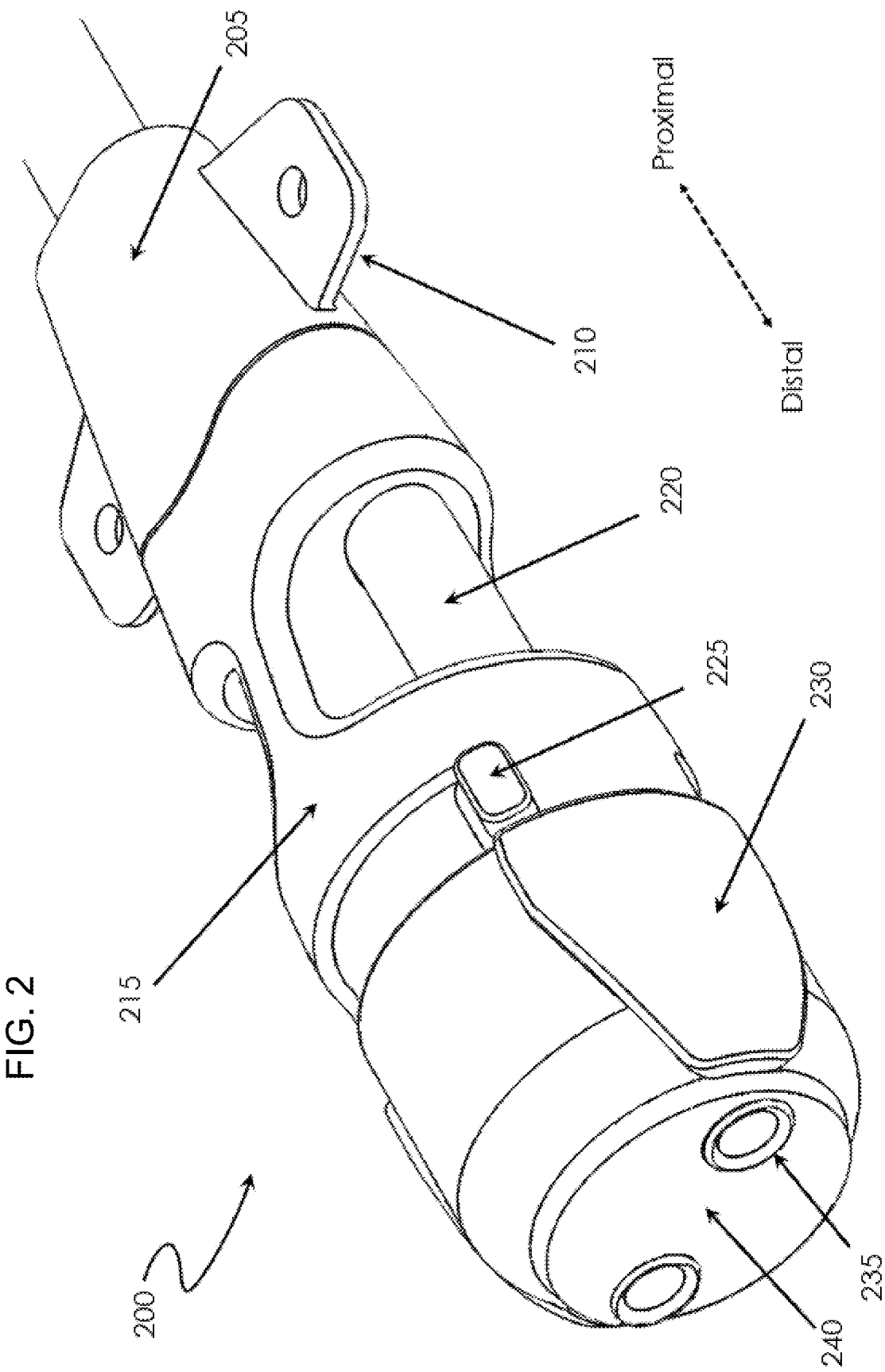
FIG. 2 illustrates a perspective view of the primary MLC assembly according to an exemplary embodiment of the present invention.

FIG. 2 illustrates a perspective view of the primary MLC assembly according to an exemplary embodiment of the present invention. As illustrated in FIG. 2, the primary MLC assembly 200 is in immediate proximity to (e.g., abutting contact with) the catheter hub 205, and where the catheter hub 205 may contain molded securement features 210. The primary MLC assembly 200 includes a semi-rigid outer housing 215 that confines the single lumen extension(s) 220 of the catheter hub 205. In the present illustration, a portion of the single lumen extension(s) 220 is visible between the proximal and distal ends of the primary MLC assembly 200, which allows for a visual check of the fluid lumen (e.g., detect air embolus, verify flushed line, etc.).

Further with respect to FIG. 2, the primary MLC assembly 200 includes at least one occluding mechanism 225 (e.g., sealing or blocking member). The occluding mechanism(s) 225 rotates axially, with respect to the catheter, and within the semi-rigid outer housing 215 to block a section (internal feature not shown) of the single lumen extension tube(s) 220. In other words, the occluding mechanism is formed as a clamp and is isolated from contact with the fluid flowing in the tubes. The occluding mechanism 225 is toggled between an open (unclamped) and closed (clamped) state by the action of an attachable secondary MLC assembly (shown in FIG. 3). The orientation features 230 on the outer housing 215 align the attachable secondary MLC assembly to the primary MLC assembly 200. The distal end of the primary MLC assembly 200 includes a direct access lumen opening 235 corresponding to each fluid lumen of the elongated medical device, and a distal surface 240 against which an attaching member seats, thereby creating a fluid-tight connection with the coupling system.

Figure 3:
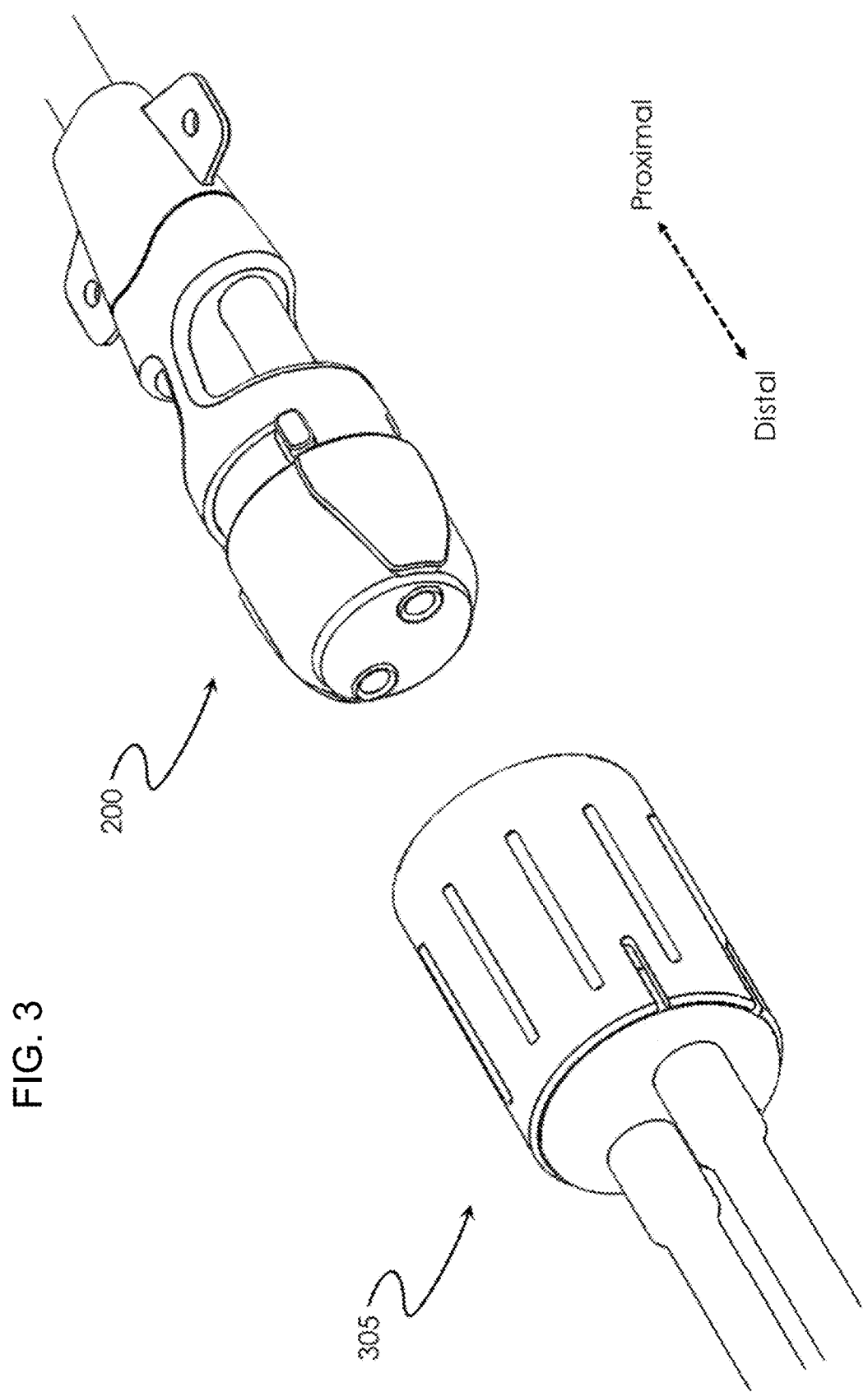
FIG. 3 illustrates an exploded view of the primary MLC assembly and an attachable secondary MLC assembly according to an exemplary embodiment of the present invention.

FIG. 3 illustrates an exploded view of the primary MLC assembly and an attachable secondary MLC assembly according to an exemplary embodiment of the present invention. The primary MLC assembly 200 is coupled to the catheter at the time of manufacture. The secondary MLC assembly 305 represents disposable attachable members with a common fluid coupling interface with the primary MLC assembly 200. Accordingly, the secondary MLC assembly 305 may be removed during the implanted lifespan of the catheter. For instance, the secondary MLC assembly 305 may consist of multiple single lumen extension tubes, each corresponding to an individual fluid lumen of the primary MLC assembly 200 (as shown in FIG. 3), where the distal end of the secondary MLC assembly 305 may include a standard medical fitting such as a Luer connector. Alternatively, the secondary MLC assembly may include a syringe with a proximal end having corresponding features to enable coupling of the fluid channel(s) between the primary MLC assembly 200 and the secondary MLC assembly 305. With respect to FIG. 3, the present invention describes proximal features of the secondary MLC assembly 305 as interfacing with distal features of the primary MLC assembly 200, where the secondary MLC assembly 305 may take on several forms and functions. Therefore, as stated previously, these exemplary embodiments provide merely a sampling of the many different forms and functions representative of attachment members that may be derived (including forms that permit clinical functions not specifically listed in this present invention but are apparent from the detailed descriptions of the features and advantages of the invention and as it is intended by the appended claims), and merely a sampling of the variety of medical articles used for fluid transfer (e.g., a syringe or infusion tubing) that could be either configured for assembly as the secondary MLC assembly 305 or attached to enabling features on the secondary MLC assembly 305 (e.g., a Luer fitting).

Figure 4:
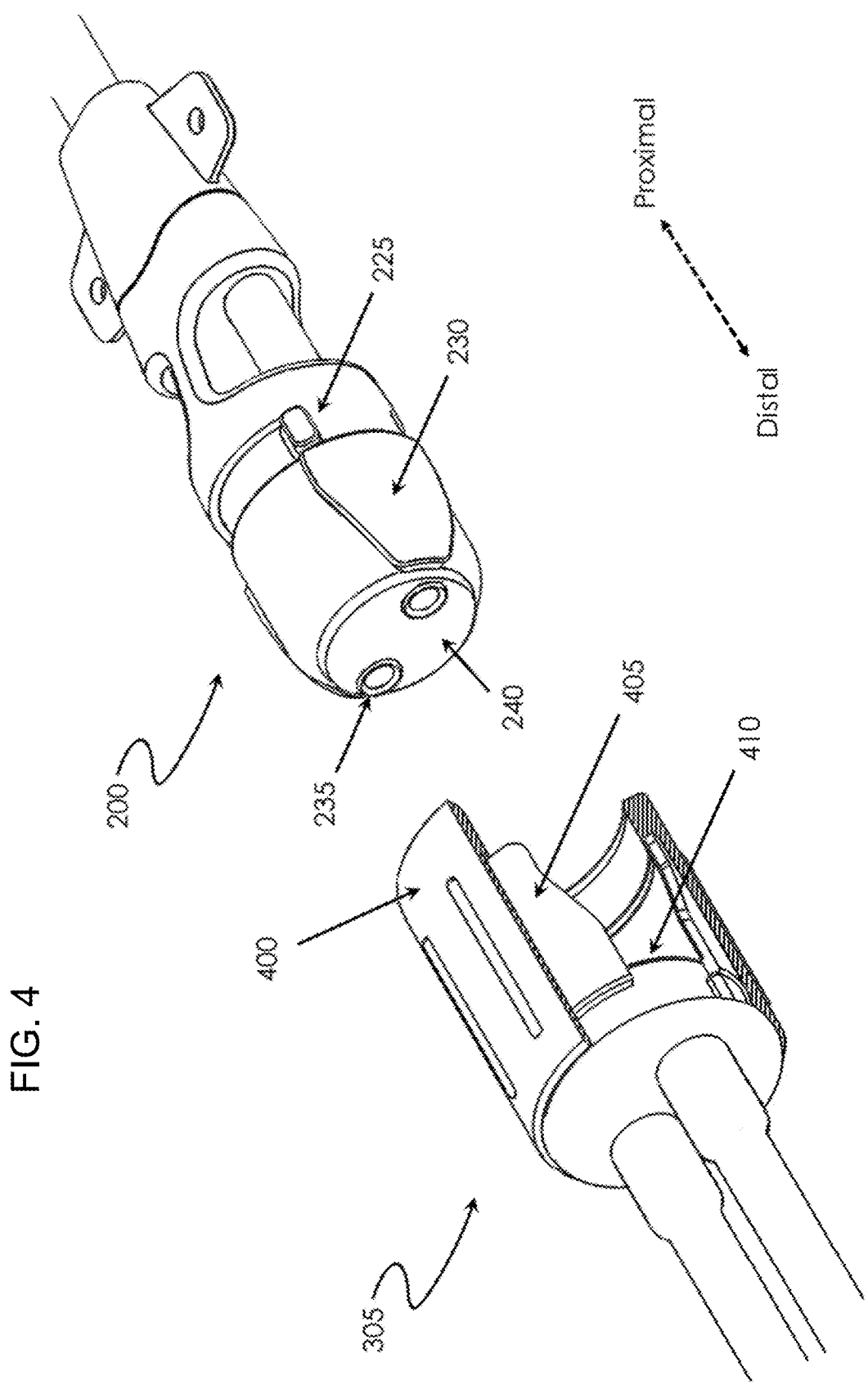
FIG. 4 illustrates a partial cross-sectional view of the attachable secondary MLC assembly according to an exemplary embodiment of the present invention.

FIG. 4 illustrates a partial cross-sectional view of the attachable secondary MLC assembly according to an exemplary embodiment of the present invention. The secondary MLC assembly 305 may include at least one outer rotating member 400 relative to a fixed alignment inner surface 405, where the alignment inner surface 405 corresponds to the orientation features 230 of the primary MLC assembly 200. The outer rotating member(s) 400 may be configured to: secure the secondary MLC assembly 305 to the primary MLC assembly 200, and toggle the position of the occluding mechanism(s) 225 to an either opened or closed status with respect to the patency of the internal fluid lumen(s). Further with regard to the function of coupling the secondary MLC assembly 305 to the primary MLC assembly 200, a proximal surface 410 of the secondary MLC assembly 305 interfaces with a distal surface 240 of the primary MLC assembly 200 to form a fluid-tight seal. According to one embodiment of the present invention, the proximal surface 410 may be elastically compressed to create a seal around the individual fluid lumen opening(s) 235. Additional details regarding the functions of the outer rotating member(s) 400 are noted in FIGS. 9A-9C, FIG. 10, and FIG. 11.

Figure 5:
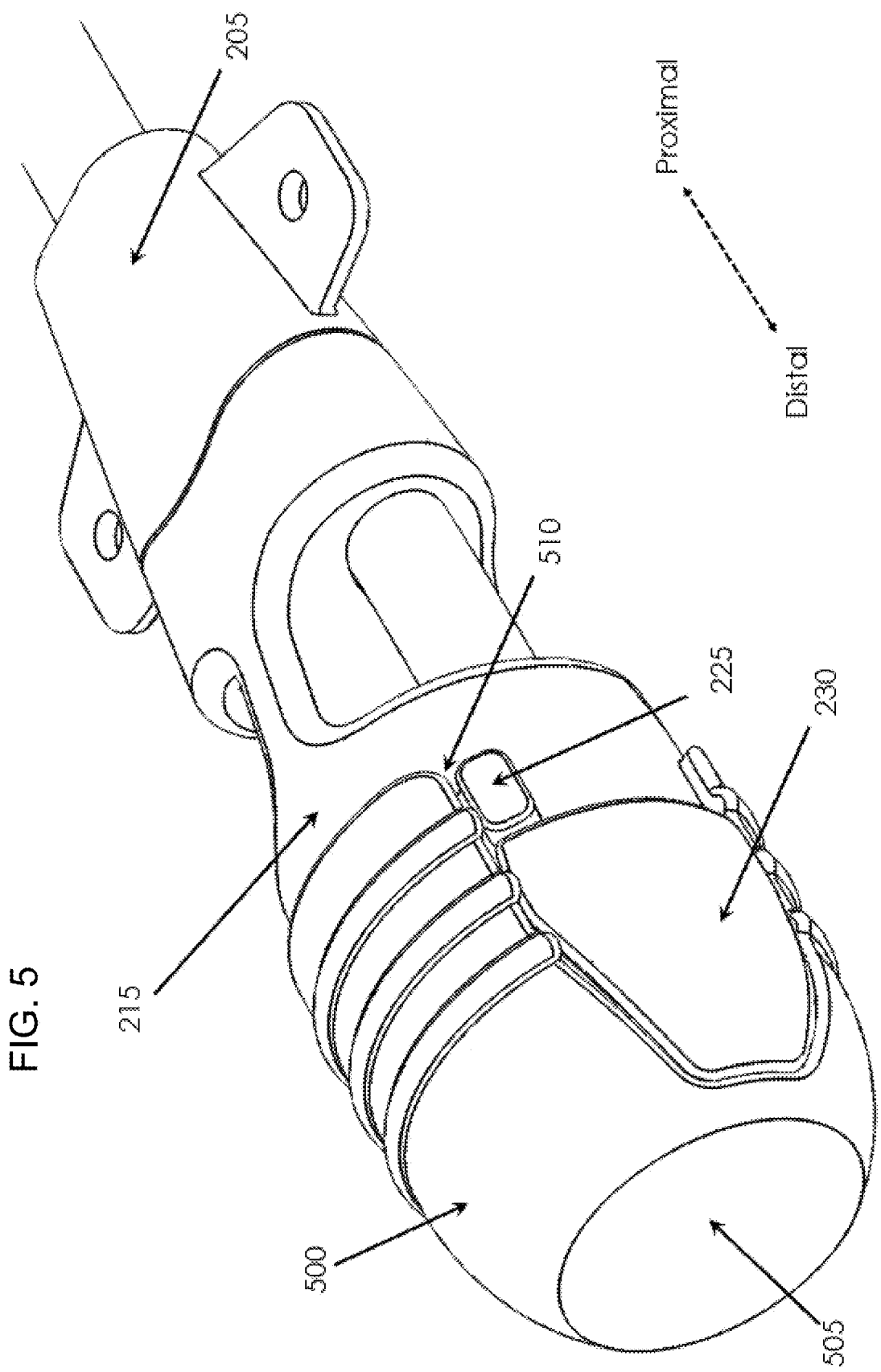
FIG. 5 illustrates a perspective view of the primary MLC assembly incorporating an attachment member for sealing the distal end of the MLC according to an exemplary embodiment of the present invention.

FIG. 5 illustrates a perspective view of the primary MLC assembly with an attached distal cap according to an exemplary embodiment of the present invention. The distal cap 500 is an example of an attachment member designed to seal the fluid lumen extension(s) of the fluid coupler when not actively in use for fluid administration. The distal cap 500 includes a solid distal surface 505 and a proximal inner surface designed to seal each individual fluid lumen of the primary MLC assembly. The distal cap 500 is aligned to the primary MLC using the orientation features 230 and disables the axial rotation of the occluding mechanism 225 when fully attached, illustrated by a proximal edge 510 positioned within the rotational path of the occluding mechanism 225. The distal cap 500 is assembled to the primary MLC assembly through a physical means such as a friction fit or interlocking mechanism such that the distal cap 500 may be removed prior to accessing the intraluminal space of the catheter for fluid administration purposes.

Figure 6:
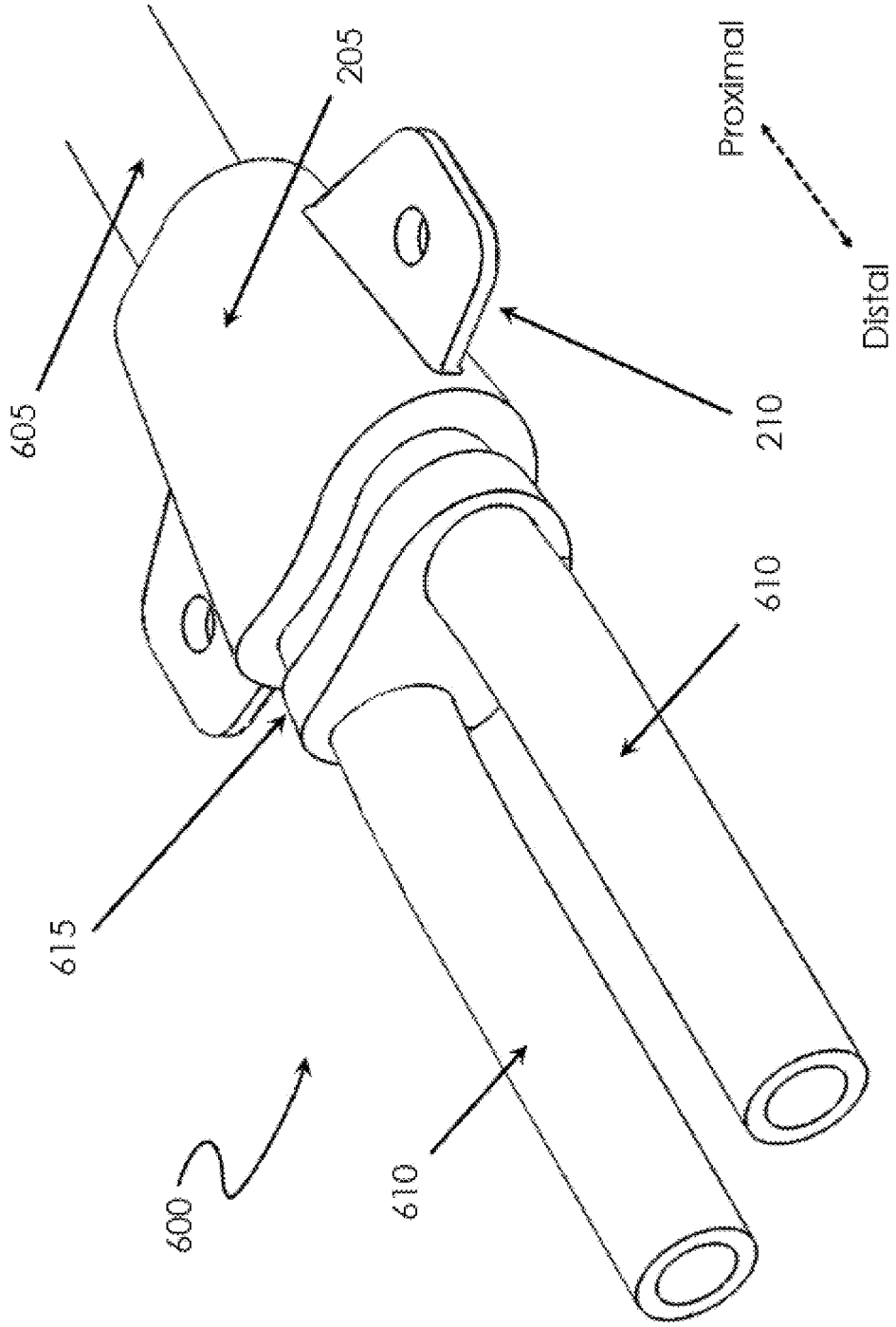
FIG. 6 illustrates the distal end of a primary catheter assembly according to an exemplary embodiment of the present invention.

FIG. 6 illustrates the distal end of a primary catheter assembly, representing an elongated medical device such as a percutaneous catheter. The figure shows the distal extravascular portion of a multi-lumen catheter 605 and a molded catheter hub 205 which bifurcates the individual fluid lumens of the multi-lumen catheter 605 into individual single lumen extensions 610 according to methods known in the art of manufacturing multi-lumen catheters. The catheter hub 205 may also include molded securement features 210 for affixing the catheter to the patient either directly or through the use of secondary securement devices. Additionally, FIG. 6 illustrates a molded region 615 of the catheter hub 205 that enables assembly of the primary MLC. This molded region 615 secures the primary MLC assembly directly to the catheter hub 205.

Figure 7:
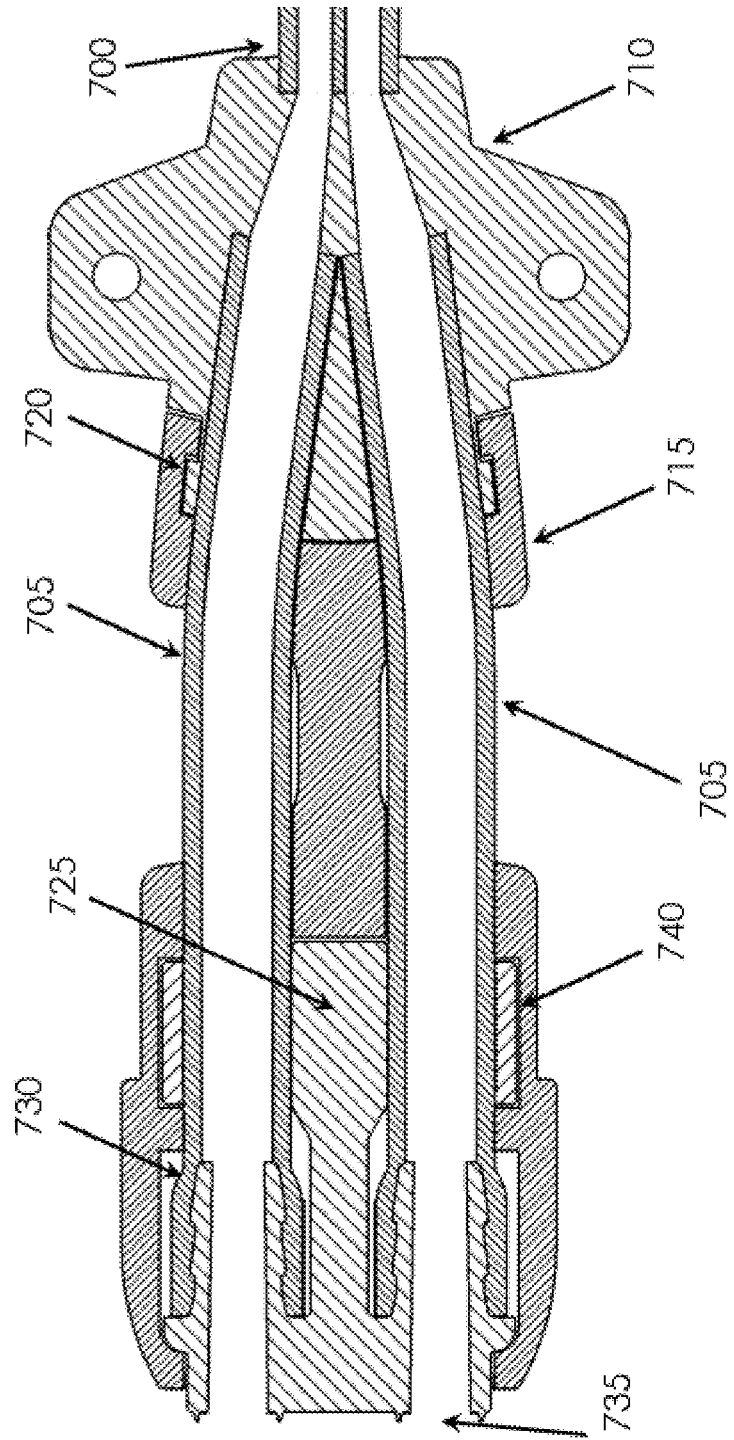
FIG. 7 illustrates a cross-sectional view of the primary MLC assembly according to an exemplary embodiment of the present invention.

FIG. 7 illustrates a cross-sectional view of the primary MLC assembly according to an exemplary embodiment of the present invention. In the present embodiment, FIG. 7 shows a multi-lumen catheter 700 joined to single lumen elastic tubing 705 via an overmold process creating the catheter hub 710 and individual fluid lumens 705. The semi-rigid housing 715 may be mounted to the catheter hub 710 via an interlocking region 720 molded in the catheter hub 710. While the assembly process of the primary MLC assembly above describes a process by which the semi-rigid housing 715 and various components may be mounted to an existing catheter hub 710 which joins single lumen elastic tubing 705 to a multi-lumen catheter 700 (cf. FIG. 1), one skilled in the art can envision a first assembly of the semi-rigid housing 715 and various components including the individual single lumen elastic tubing 705 subsequently joined to a multi-lumen catheter 700 via an overmold process to create a catheter hub 710.

Further, with respect to FIG. 7, the semi-rigid housing 715 contains a rigid tube connector 725. A proximal surface of the rigid tube connector 725 is joined to a distal end 730 of the single lumen elastic tubing 705, where a distal surface 735 of the rigid tube connector 725 helps enable the direct (i.e., unobstructed) connection between an attachment member (not shown) to the individual fluid lumen(s) of the elongated medical device 700.

Accordingly, this embodiment of the present invention permits a clinician to administer an agent (e.g., a pharmaceutical) into the indwelling catheter and primary MLC assembly such that every fluid-contacting surface within the catheter assembly is available for interacting with the administered agent. As such, the catheter assembly does not impede the use of a catheter lock (i.e., a fluid solution that remains in the catheter for an extended duration, often used for anti-clotting or anti-microbial purposes) as it may be applied common to the art.

The semi-rigid housing 715 illustrated in FIG. 7 may also include an occluding mechanism 740 axially aligned in the present exemplary embodiment. The occluding mechanism 740 operates in a clamping fashion around the individual fluid lumen(s) 705 and in combination with the tube connector 725 (discussed further in FIG. 8).

FIGS. 8A-8B illustrate perspective views of various positions of the occluding mechanism. In an exemplary embodiment of the present invention, the rigid tube connector 115 has a generally ellipsoid geometrical shape having a major diameter 800 and a minor diameter 805. Likewise, an inner surface of the occluding mechanism 120 has a generally ellipsoid geometrical shape having a major diameter 810 and a minor diameter 815. The occluding mechanism 120 is illustrated by two distinct resting positions: FIG. 8A and FIG. 8B.

Recalling the tandem alignment of the two single lumen extensions of the catheter subassembly 100 with respect to the spatial orientation of the tube connector 115 in FIG. 1, FIG. 8A illustrates a closed (clamped) state of the occluding mechanism 120. Specifically, the single lumen extension tubing (not shown) is compressed between the minor diameter 815 of the occluding mechanism 120 and the minor diameter 805 of the tube connector 115. FIG. 8B illustrates an open (unclamped) state of the occluding mechanism 120. Specifically, the single lumen extension tubing (not shown) is not compressed due to the alignment of the major axis 810 of the occluding mechanism with the minor axis 805 of the tube connector 115, with the single lumen tubing uncompressed between the two surfaces. Rotation of the occluding mechanism 120 between FIG. 8A and FIG. 8B is accomplished by an action of the secondary MLC assembly (not shown).

With respect to FIG. 8, while the geometrical design illustrated may characterize features of the occluding mechanism as shapes generally of an elliptical nature, the present disclosure is not limited thereto and may include a variety of designs that could accomplish a similar occluding function whether symmetrical or asymmetrical, centered axially or off-set, or for single or multiple clamping regions (i.e., multiple occluding mechanisms (see FIG. 11) and/or multiple fluid lumens). Moreover, while FIG. 8 illustrates a combined clamping action between the occluding mechanism 120 and the tube connector 115, the present disclosure is not limited thereto and the occluding mechanism may function in isolation of or in combination with any other rigid member of the primary MLC assembly.

Figure 9A:
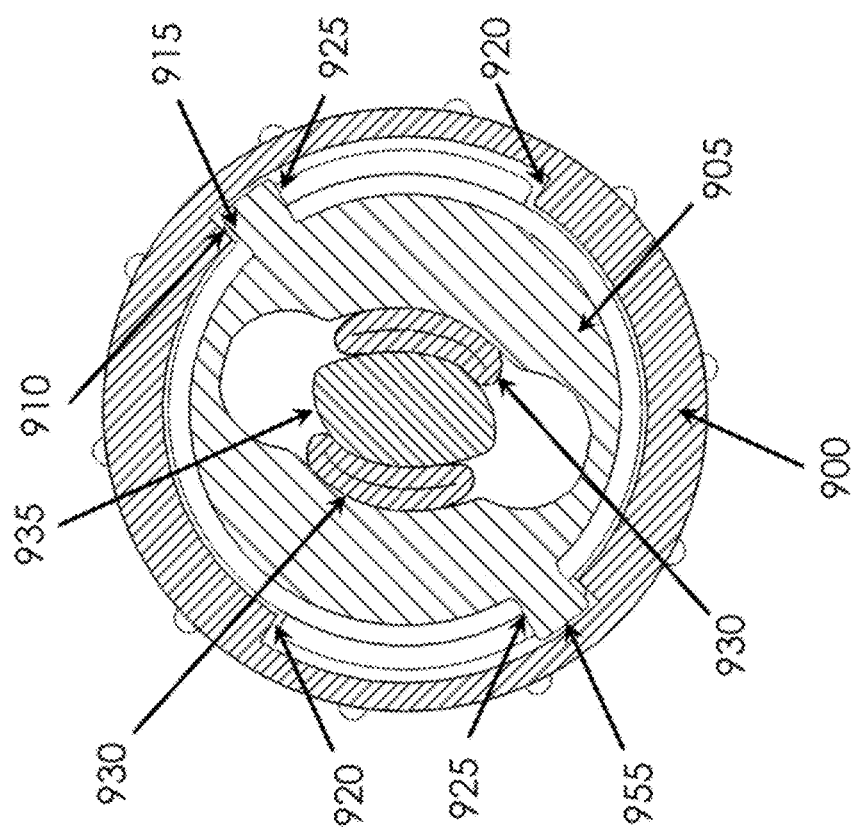
Figure 9B:
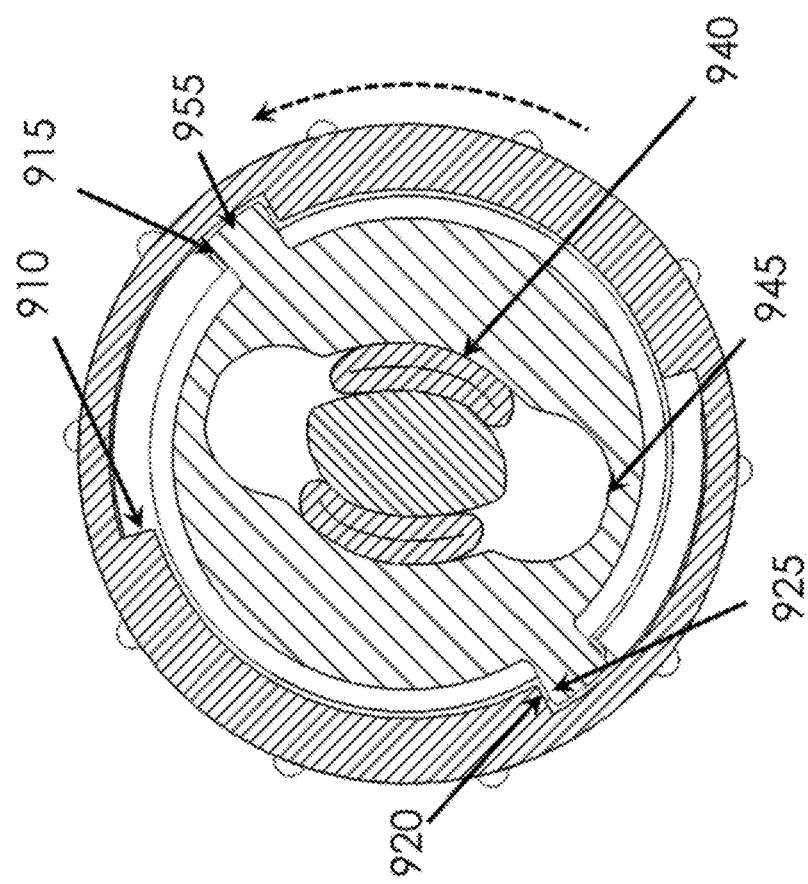

FIG. 9A-9C illustrate cross-sectional views of three distinct resting positions of a component of the secondary MLC assembly with respect to the action of the occluding mechanism (the cross-sectional orientation is from the perspective of distal looking proximal). FIG. 9A illustrates the initial attachment state where the secondary MLC assembly is attached to the primary MLC assembly through the orientation features of coupling (see FIG. 4). The occluding mechanism 905 is axially aligned inside an outer rotating member 900 of the secondary MLC assembly. The inner surface of the rotating member 900 has a leading edge 910 and a trailing edge 920, and a protrusion 955 of the occluding mechanism 905 likewise has a leading edge 915 and a trailing edge 925. Upon initial attachment (FIG. 9A), the leading edge 910 of the rotating member 900 and the leading edge 915 of the protrusion 955 of the occluding mechanism 905 are together (e.g., disposed at same location), while the respective trailing edges 920 and 925 are spaced apart. In this configuration, the single lumen tubing 930 is clamped between the occluding mechanism 905 and a surface on the tube connector 935.

FIG. 9B illustrates a partial rotation of the rotating member 900, resulting in no change of position of the occluding mechanism 905 (i.e., lost motion) and a separation of the leading edge 910 of the rotating member 900 and leading edge 915 of the protrusion 955 of the occluding mechanism 905. Accordingly, the trailing edge 920 of the rotating member 900 and the trailing edge 925 of the protrusion 955 of the occluding mechanism 905 are brought together. This partial rotation results in a locking action to secure the secondary MLC assembly to the primary MLC assembly (see FIG. 4 and FIG. 10). During this locking action, the single lumen tubing 930 remains compressed by the minor axis 940 of the occluding mechanism 905. FIG. 9B illustrates an important stage of the coupling system wherein the fluid lumen(s) of the primary catheter assembly remain closed until the secondary MLC assembly is fully seated and establishes a fluid-tight connection (cf. FIG. 10).

FIG. 9C illustrates the final rotational position of the rotating member 900, where the occluding mechanism 905 has been rotated such that the major axis 945 of the occluding mechanism 905 is oriented to allow the single lumen tubing to be in an uncompressed state (e.g., open and returned to an initial state) 950. Rotation of the occluding mechanism 905 results from a translation of the rotating force applied to the rotating member 900 through the trailing edge 920 to the trailing edge 925 of the protrusion 955 of the occluding mechanism 905. Accordingly, the function of opening or closing the occluding mechanism is performed by an action of the attachable secondary MLC assembly.

Although not illustrated in FIGS. 9A-9C, the detachment of the secondary MLC assembly follows a generally reverse sequence of events. Beginning with FIG. 9C, rotation of rotating member 900 in the clockwise direction generates lost motion from the separation of the trailing edge 920 of the rotating member 900 and the trailing edge 925 of the protrusion 955 of the occluding mechanism 905; the occluding mechanism 905 remains unmoved. Continued rotation of the rotating member 900 imparts a rotational force from the leading edge 910 of the rotating member 900 to the leading edge 915 of the protrusion 955 of the occluding mechanism 905. The rotating member 900 is turned clockwise until reaching the initial state in FIG. 9A, where the single lumen tubing 930 is clamped and the orientation features (not shown) allow detachment of the secondary MLC assembly. Accordingly, the design of this present invention results in an embedded safety feature through the implicit clamping of the single lumen extensions tubing(s) prior to the detachment of the secondary MLC assembly.

Figure 10:
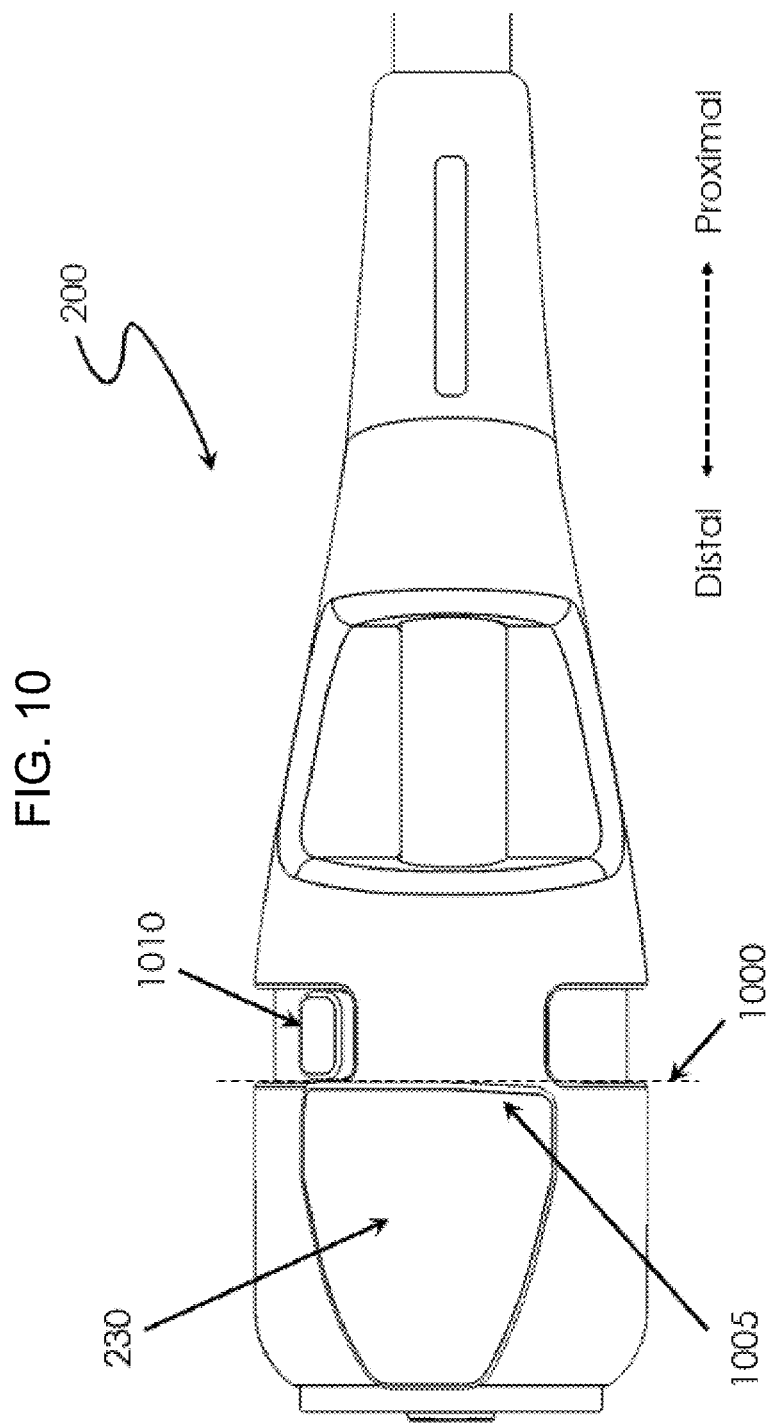
FIG. 10 illustrates a profile view of the primary MLC assembly to highlight a feature that supports an aspect of the mechanical system that couples the primary MLC assembly and attachable secondary MLC assembly according to an exemplary embodiment of the present invention.

FIG. 10 illustrates a profile view of the primary MLC assembly to highlight a feature that supports an aspect of the coupling between the primary MLC assembly and attachable secondary MLC assembly according to an exemplary embodiment of the present invention. As addressed earlier, the primary MLC assembly 200 contains orientation features 230 to align the attachable secondary MLC assembly (not shown) to the primary MLC assembly 200 during coupling between the assemblies. Recalling FIG. 9A, initial attachment of the secondary MLC assembly corresponds to a non-secure but correctly oriented attachment of the coupling system. In an exemplary embodiment of the present invention, the orientation feature 230 additionally includes a non-tapered edge 1000 (contiguous with and identified by the overlaid vertical dashed line) and a tapered edge 1005 orthogonal to the axis of rotation of a rotating member of the attachable secondary MLC assembly. The tapered edge 1005 is initially engaged by an internal surface of the rotating member (not shown) which draws the distal surface of the primary MLC assembly 200 closer to a proximal surface of the attachable secondary MLC assembly to achieve a more secure fluid-tight connection (cf. FIG. 9B; see also the description to FIG. 4). Upon a secure attachment, the rotating member maintains positional relationship, with regard to distal/proximal position, along the non-tapered edge 1000. With respect to FIG. 10, engagement of the rotating member of the attachable secondary MLC assembly with a feature of the occluding mechanism 1010 occurs during the engagement with the non-tapered surface 1000 (cf. FIG. 9C).

Figure 11:
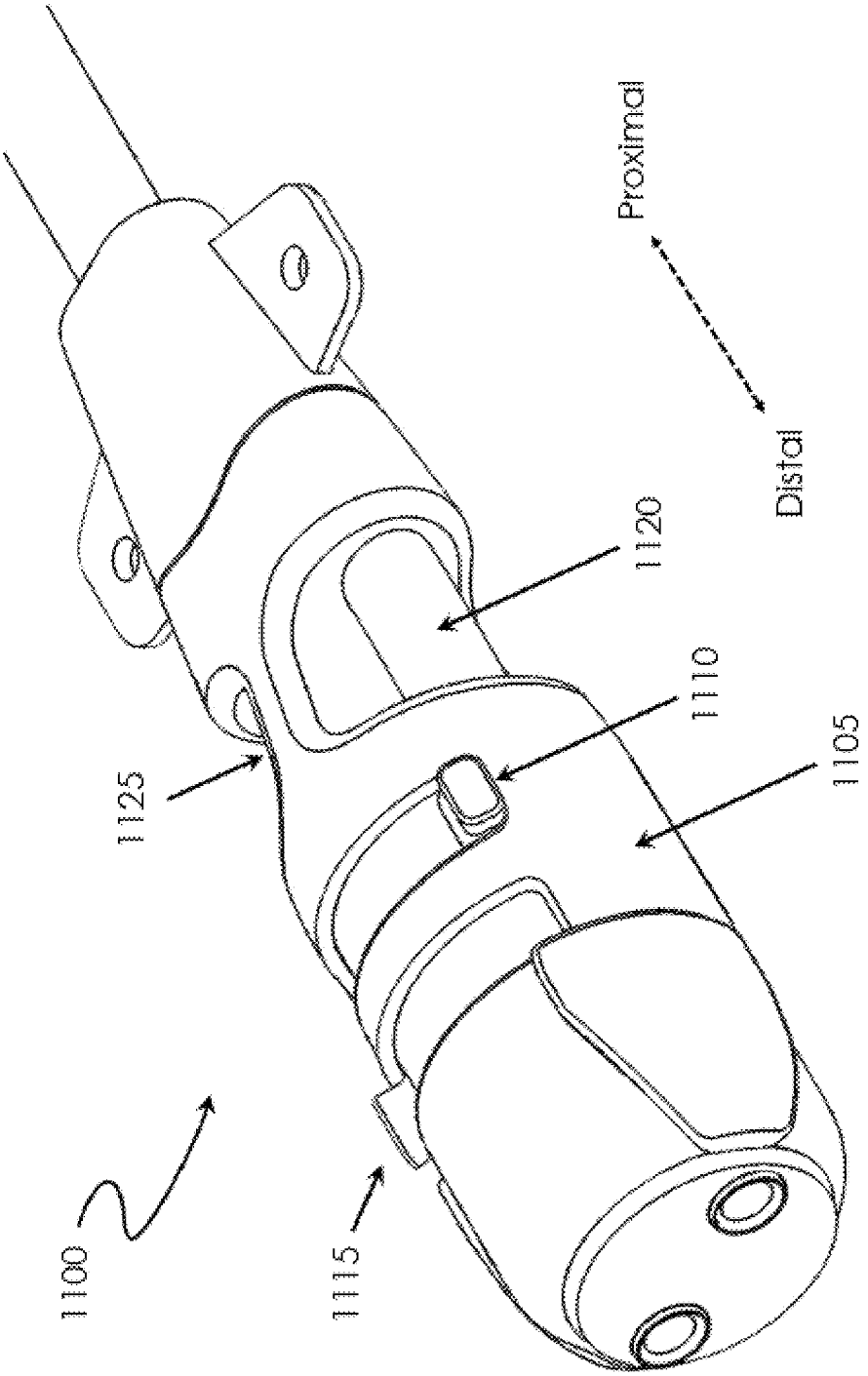
FIG. 11 illustrates a perspective view of a primary MLC with multiple occluding mechanisms according to another exemplary embodiment of the present invention.

FIG. 11 illustrates a perspective view of a primary MLC assembly with multiple occluding mechanisms according to another exemplary embodiment of the present invention. As illustrated in FIG. 11, the primary MLC assembly 1100 may include a first occluding mechanism 1110 corresponding to a first single lumen extension tube 1120, and a second occluding mechanism 1115 corresponding to a second single lumen extension tube 1125 (not visible from perspective) within the outer housing 1105. Accordingly, the attachable secondary MLC assembly may include at least two rotating members, each corresponding to an action of opening/closing the occluding mechanisms 1110 and 1115 of the primary MLC assembly. In this manner, a clinician may selectively open one fluid lumen of the primary catheter assembly while maintaining the other fluid lumen(s) of the primary catheter assembly in an occluded (closed) state.

With respect to the illustrations and descriptions above, references to single lumen extensions or elastic tubing are intended to be more broadly defined as a non-rigid material either existing as distinct members (i.e., individual tubes) or a single member with individual lumens. Therefore, the occluding mechanism conveyed by the present invention may include a spectrum of approaches ranging from the illustrations provided herein applicable to individual extension tubes or a single elastic member with a depressible region that, when depressed, forms a fluid-tight obstruction, and which are disposed between the proximal end and distal end of the primary MLC assembly. Particularly, the present disclosure advantageously provides a fluid-tight connection between a primary MLC assembly and a secondary MLC without the opening of a fluid path. Thus, the fluid path is capable of being blocked prior to breaking such a fluid-tight connection when the secondary MLC assembly is detached from the primary MLC assembly.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A multi-lumen coupling system, comprising:
a primary multi-lumen coupler (MLC) assembly;
a secondary MLC assembly attachable to the primary MLC assembly; and
an occluding mechanism disposed between a proximal end and a distal end of the primary MLC assembly to block fluid flow therebetween,
wherein the occluding mechanism is configured to block fluid flow in the primary MLC assembly prior to a detachment of the secondary MLC assembly from the primary MLC assembly by a rotation of the secondary MLC assembly.

2. The multi-lumen coupling system of claim 1, wherein after attachment of the secondary MLC assembly to the primary MLC assembly, the occluding mechanism is moved from a closed state to an open state.

3. The multi-lumen coupling system of claim 2, wherein the primary MLC assembly is in abutting contact with a catheter hub at the proximal end of the primary MLC assembly and wherein the primary MLC assembly includes:
an outer housing that confines at least one single lumen extension tube to the catheter hub;
a tube connector connected at a distal end of the outer housing; and
the occluding mechanism disposed between the outer housing and the tube connector.

4. The multi-lumen coupling system of claim 3, wherein the distal end of the primary MLC assembly defines an opening into an interior of the outer housing of the primary MLC assembly and the proximal end of the primary MLC assembly defines a proximal connector that couples to the catheter hub.

5. The multi-lumen coupling system of claim 4, wherein the catheter hub includes a single lumen extension tube or multiple single lumen extension tubes.

6. The multi-lumen coupling system of claim 5, wherein a proximal end of the secondary MLC assembly connects to the distal end of the primary MLC assembly and a distal end of the secondary MLC assembly includes a fluid fitting.

7. The multi-lumen coupling system of claim 6, wherein the fluid fitting is a Luer connector.

8. The multi-lumen coupling system of claim 6, wherein the secondary MLC assembly includes a single lumen extension tube that corresponds to the single lumen extension tube of the primary MLC assembly.

9. The multi-lumen coupling system of claim 8, wherein a proximal end of the single lumen extension tube of the secondary MLC assembly forms a fluid-tight seal with a corresponding opening on a distal connector of the primary MLC assembly.

10. The multi-lumen coupling system of claim 6, wherein the secondary MLC assembly includes two or more single lumen extension tubes and a proximal end of each single lumen extension tube couples to a single connector interface.

11. The multi-lumen coupling system of claim 10, wherein the single connector interface is releasably engaged with a distal connector of the primary MLC assembly to couple each single lumen extension tube of the second MLC assembly to a corresponding single lumen extension tube of the primary MLC assembly.

12. The multi-lumen coupling system of claim 6, wherein the fluid fitting provides a fluid channel between an attachable member and the distal end of the secondary MLC assembly.

13. The multi-lumen coupling system of claim 4, wherein the single lumen extension tube extends between the proximal end and the distal end of the primary MLC assembly.

14. The multi-lumen coupling system of claim 13, wherein the occluding mechanism blocks a portion of a fluid channel of the single lumen extension tube.

15. The multi-lumen coupling system of claim 3, wherein in the closed state of the occluding mechanism, the single lumen extension tube is compressed between the occluding member and the tube connector and in the open state of the occluding mechanism, the single lumen extension tube is uncompressed due to rotated alignment of the occluding member in relation to the tube connector.

16. The multi-lumen coupling system of claim 3, wherein the primary MLC assembly includes orientation features formed on the outer housing and wherein the secondary MLC assembly includes at least one rotating member relative to a fixed alignment inner surface which corresponds to the orientation features of the primary MLC assembly to align the primary and second MLC assemblies and axially align the occluding mechanism inside the rotating member.

17. The multi-lumen coupling system of claim 16, wherein an inner surface of the at least one rotating member includes a leading edge and a trailing edge and wherein a protrusion formed on the occluding mechanism includes a leading edge and a trailing edge.

18. The multi-lumen coupling system of claim 17, wherein in an initial attachment state of the primary and secondary MLC assemblies, the leading edge of the at least one rotating member and the leading edge of the protrusion are disposed proximate to each other and the trailing edge of the at least one rotating member and the trailing edge of the protrusion are spaced apart while the at least one single lumen extension tube remains clamped between the occluding mechanism and the tube connector.

19. The multi-lumen coupling system of claim 18, wherein in a partial rotation state of the at least one rotating member, the leading edge of the at least one rotating member and the leading edge of the protrusion are separated and the trailing edge of the at least one rotating member and the trailing edge of the protrusion are brought together to secure the secondary MLC assembly to the primary MLC assembly while the at least one single lumen extension tube remains clamped between occluding mechanism and the tube connector.

20. The multi-lumen coupling system of claim 19, wherein in a final rotation state of the at least one rotating member, the trailing edge of the at least one rotating member and the trailing edge of the protrusion remain together to release the at least one single lumen extension tube and open a flow channel therein.

21. The multi-lumen coupling system of claim 1, further comprising:
an attachment member connected to the distal end of the primary MLC assembly to seal the system.

22. The multi-lumen coupling system of claim 21, wherein the attachment member connects to the distal end of the primary MLC assembly and is secured by a locking member, and wherein the attachment member blocks rotation of a protrusion that is formed on the primary MLC assembly and that engages with the secondary MLC assembly.

\* \* \* \* \*